United States Patent
Levecq et al.

(10) Patent No.: US 9,532,713 B2
(45) Date of Patent: Jan. 3, 2017

(54) METHOD AND DEVICE FOR HIGH-RESOLUTION RETINAL IMAGING

(75) Inventors: Xavier Levecq, Gif sur Yvette (FR); Barbara Lamory, Palaiseau (FR)

(73) Assignee: Imagine Eyes, Orsay (FR)

( * ) Notice: Subject to any disclaimer, the term of this patent is extended or adjusted under 35 U.S.C. 154(b) by 580 days.

(21) Appl. No.: 13/983,068

(22) PCT Filed: Jan. 27, 2012

(86) PCT No.: PCT/EF2012/051327
§ 371 (c)(1),
(2), (4) Date: Aug. 1, 2013

(87) PCT Pub. No.: WO2012/104211
PCT Pub. Date: Aug. 9, 2012

(65) Prior Publication Data
US 2013/0308098 A1 Nov. 21, 2013

(30) Foreign Application Priority Data
Feb. 1, 2011 (FR) ..................................... 11 50760

(51) Int. Cl.
*A61B 3/14* (2006.01)
*A61B 3/10* (2006.01)
(Continued)

(52) U.S. Cl.
CPC ............... *A61B 3/14* (2013.01); *A61B 3/1015* (2013.01); *A61B 3/1225* (2013.01)

(58) Field of Classification Search
CPC ........... A61B 3/14; A61B 3/103; A61B 3/113; A61B 3/135; A61B 3/1225; A61B 3/024; A61B 3/1015
(Continued)

(56) References Cited

U.S. PATENT DOCUMENTS

2004/0207811 A1  10/2004  Elsner
2007/0030447 A1*  2/2007  Yamaguchi .......... A61B 3/1015
                                                  351/206
2007/0258045 A1  11/2007  Yamaguchi et al.

OTHER PUBLICATIONS

International Search Report issued in PCT/EP2012/051327 mailed on Mar. 21, 2012 (6 pages).
(Continued)

*Primary Examiner* — Dawayne A Pinkney
(74) *Attorney, Agent, or Firm* — Osha Liang LLP

(57) ABSTRACT

The invention relates to a high-resolution retinal imaging method and device notably comprising an emission source (LSr) for emitting a light beam for the illumination of the retina of an eye (10) of a subject, a detection device (12) capable of detecting spatial-frequency structures of 250 cycles/mm measured in the plane of the retina, an optical imaging system (16) allowing for the formation of an image of at least a part of the retina on the detection device (12), a device (15) for measuring optical defects with an analysis plane of the optical defects, a correction device (14) comprising a correction plane and intended to correct, in said correction plane, the light rays from said emission source (LSr) and backscattered by the retina as a function of the optical defects measured by the measurement device (15). The correction and analysis planes are optically conjugated with a predetermined plane (17) of the eye, and the input pupil of said optical imaging system has a diameter of between a first value $\Phi$min and a second value $\Phi$max, the first value being defined to allow for the detection by said detection device (12), at an imaging wavelength, of structures of the retina exhibiting a spatial frequency of 250 cycles per millimeter, and the second value being less than 5.75 mm.

16 Claims, 9 Drawing Sheets

(51) Int. Cl.
*A61B 3/00* (2006.01)
*A61B 3/12* (2006.01)

(58) Field of Classification Search
USPC .................. 351/206, 200, 205, 209–210, 214,351/221–222, 246
See application file for complete search history.

(56) References Cited

OTHER PUBLICATIONS

Written Opinion of the International Searching Authority issued in PCT/EP2012/051327 mailed on Mar. 21, 2012 (7 pages).
Roorda, A. et al.; "Adaptive optics scanning laser ophthalmoscopy"; Optics Express, vol. 10, No. 9, May 6, 2002, pp. 405-412 (8 pages).
Zawadzki, R. J. et al.; "Adaptive-optics optical coherence tomography for high-resolution and high-speed 3D retinal in vivo imaging"; Optics Express, vol. 13, No. 21, Oct. 17, 2005, pp. 8532-8546 (15 pages).

* cited by examiner

METHOD AND DEVICE FOR HIGH-RESOLUTION RETINAL IMAGING

PRIOR ART

Technical Field of the Invention

The present invention relates to a high-resolution retinal imaging method and device compatible with imaging on a cellular scale.

Prior Art

These days, several years elapse between the start of a retinal disease and its diagnosis. This is because retinal diseases generally develop silently, causing irreversible lesions before the first clinical symptoms appear. Such is the case, for example, with Age-Related Macular Degeneration (ARMD) or glaucoma, a sickness that attacks the nerve fibers of the retina and that can cause blindness in the patient, and which is generally diagnosed when half the nerve fibers are irreparably destroyed. Now retinal diseases can be diagnosed as early as the first weeks if the retina can be imaged on a cellular scale. In practice, the first effects of retinal sicknesses affect the microscopic structures of the retina. The microstructures affected by the three retinal diseases that are most common and that are among the most serious (ARMD, glaucoma, diabetic retinopathy) are the photoreceptors, including the cones, photosensitive cells which detect light and which have a size varying between 2 and 5 μm, the micro-capillaries of the retina which are the smallest vessels of the human body (approximately 6 μm in diameter), and the nerve fiber bundles which have a diameter of approximately 10 μm.

Many laboratories are working on different technologies which would make it possible to carry out retinal imaging with a cellular resolution. These various technologies employ different retina illumination and/or detection systems, but all of them implement an adaptive optical system that makes it possible to measure the optical defects of the eye and of the imaging system and to correct the light rays reflected from the retina and incident on the detection system in order to increase resolution.

FIG. 1A represents a block diagram of a retinal imaging system based on adaptive optics scanning laser opthalmoscopy, or AOSLO, technology. The AOSLO assembly mainly comprises a system 11 for illuminating the retina or <<illumination block>>, a detector block 12, a scanning block 13, a correction system 14 comprising a correction plane for the incident light rays, a system for measuring the optical defects 15 comprising a plane for analyzing optical defects of incident light rays and an imaging optic 16. The illumination block comprises, for example, a laser diode coupled to an optical fiber to form a point source and an optical lens that makes it possible to form, from the point source, a lighting beam. A diaphragm of the illumination block 11 defines a pupil. The lighting beam is sent, for example by a set of mirrors (not represented), to the correction system 14, for example a deformable mirror, then into the scanning block 13 to be directed according to a vertical and horizontal scanning in the eye 10 of a subject. The lighting beam is thus focused to form, on the retina, a quasi-point beam which scans the retina and the light backscattered by the retina is subjected to the same optical scanning on return to be sent to the deformable mirror 14 and the detector block 12, comprising, for example, a confocal detection hole and a detector which can be a photo multiplier or an avalanche photodiode. A set of optical elements symbolized by the optic block 60 is involved in optically conjugating the plane of the retina and the confocal detection hole of the detector.

The system for measuring the optical defects 15 comprises, for example, an analyzer of the Shack-Hartmann type; it receives the light backscattered by the retina and controls the deformable mirror in order to correct the lighting beam and the backscattered beam. The plane of the pupil of the illumination block, the plane of the deformable mirror and the analysis plane of the system for measuring the optical defects are optically conjugated with a predetermined plane 17 of the eye, for example the pupil plane of the eye. The predetermined plane 17 is advantageously the plane of the input pupil of the retina imaging system on the detector block. The paper by A. Roorda et al. ("Adaptive optics scanning laser ophthalmoscopy", Optics express 405, Vol. 10, No 9, 2002) describes, for example, a device as schematically represented in FIG. 1A.

Hereinafter in the description, the expression "optical defects" should be understood to mean all the disturbances that the light rays undergo between the retina and the detector. These defects comprise the defects imparted by the optical system of the eye but also by the optical system of the imaging system.

The expression "input pupil" of an optical system should be understood to mean the smallest aperture which limits the entry or the propagation of the light rays in the system. This aperture can be real in the case where a physical diaphragm, the pupil of the optical system concerned, limits the entry of the light rays, or virtual in the case where this aperture is an image of the physical pupil of the optical system which is located inside the optical system and which is formed, for example, by a diaphragm. Thus, in the case where the retina imaging system 16 is positioned in the pupil plane of the eye or in a plane situated in proximity thereto, said input pupil is virtual, the image of a physical diaphragm situated inside said optical imaging system.

FIG. 1B represents a theoretical block diagram of an assembly of OCT (Optical Coherence Tomography) type coupled to the adaptive optic. Such a system is described, for example, in R. Zawadzki ("Adaptive-optics optical coherence tomography for high resolution and high speed 3D retinal in vivo imaging", Optics Express 8532, Vol. 13, No 21, 2005). OCT relies on the use of an interferometer with low coherence. This imaging technique makes it possible to produce, in vivo, cross-sectional images of tissues, with a resolution of a few microns. One of the interests in using OCT in ophthalmology lies in its capacity to reveal, in-vivo, tissues through other diffusing tissues. The assembly of FIG. 1B gives a very simplified view of the main elements of an assembly of OCT type. The arrangement is similar to that of AOSLO but, here, the detector block 12 is specific to the OCT and notably comprises an interferometer, for example a fibered interferometer, for example of Michelson type. The input point of the fiber (not represented) is conjugated with the retina of the eye 10 by means of an optical conjugation system symbolized by the optic 16. Compared to AOSLO, the OCT technology makes it possible to image a longitudinal cross section of the retina to the detriment of acquisition speed.

FIG. 1C represents a theoretical block diagram of a full-field, or "flood", retinal imaging system, described, for example, in "Adaptive Optics Ophthalmoscopy" by A. Roorda (Journal of Refractive Surgery Vol. 16 September/October 2000) or in H. Hofer et al. ("Improvements in retinal image quality with dynamic correction of the eye's aberrations", Optics Express, Vol. 8, Issue 11, pp. 631-643, 2001). In this system, the illumination block comprises a first, extended, emission source for the imaging, and a second, point emission source for the analysis of the optical defects. The detector block 12 comprises a multi-detector acquisition device (or matrix detector), for example a CCD camera, the detection plane of which is intended to be optically conjugated with the retina of the eye 10 that is to be imaged, using an optical image-forming system—or imaging system—symbolized by the optics 16. A system for measuring optical defects 15, for example of Shack-Hartmann analyzer type, analyses the optical defects undergone by the rays from the analysis source and backscattered by the retina. It is linked to a correction system 14, for example a deformable mirror, in order to correct the light rays backscattered by the retina. As in the systems described previously, the analysis plane of the system for measuring the optical defects and the plane of the deformable mirror are optically conjugated with a predetermined plane of the eye, for example the pupil plane 17 of the eye which is advantageously the plane of the input pupil of the retina imaging system on the detector 12. The device thus described with reference to FIG. 1C, while it is limited in depthwise exploration of the retina, does, however, compared to the systems of OCT or AOSLO type, present the advantage of operating in full-field mode, that is to say without mechanical scanning of the retina, and with much shorter full image acquisition times, which makes it at the same time less complex to produce, less costly and less sensitive to the deformations that the image undergoes during the acquisition time, deformations which are generated by the movement of the retina.

In each of these devices, an imaging system 16 makes it possible to form the image of the retina on a detector block 12 designed to allow for the detection of spatial frequency structures of the order of 250 cycles/mm on the retina, forming an imaging path. A correction device 14, for example a deformable mirror, comprising a correction plane for the light rays backscattered by the retina, controlled by a system for measuring optical defects 15, makes it possible to correct all or part of the optical defects due to the eye and to the optical system of the imaging system and thus enhance the quality of the image of the retina formed on the detection block 12. The system for measuring the optical defects makes it possible to determine, in an analysis plane and in a single measurement, the optical defects of an incident light wave. It is advantageously an analyzer of Shack-Hartmann type comprising an analysis plane formed by a set of microlenses and a matrix detector arranged in the focal plane of said microlenses. In these systems, the analysis plane of the analyzer of the optical defects and the correction plane of the correction device are optically conjugated with a predetermined plane of the input space of the imaging system, a real plane intended to be merged with a predetermined plane of the eye, for example the pupil plane of the eye. The input pupil of the imaging system is advantageously situated in this same predetermined plane. The analysis path is thus formed by the system for measuring optical defects 15 and means for conjugating the analysis plane with said predetermined plane in the input space of the imaging system. The input pupil of the imaging system is, for example, an image of the physical pupil of the correction device, formed, for example, by a diaphragm and defining the useful surface of the correction device.

It is common practice to try to make the size of the input pupil of the imaging system between the retina and the detector as large as possible, both to gain in resolution and to maximize the light flux coming from the pupil of the eye and therefore benefit from a better signal-to-noise ratio.

The applicant has shown that, contrary to the expected effect, limiting the size of the pupil to a certain extent made it possible to enhance the quality of the image by significantly enhancing the signal-to-noise ratio, this being due notably to the nature of the light backscattered by the retina.

SUMMARY OF THE INVENTION

According to a first aspect, the invention relates to a high-resolution retina imaging device comprising:
- at least one emission source for emitting a light beam for the illumination of the retina of an eye of a subject, emitting in a given range of imaging wavelengths,
- a retina imaging path comprising a detection device capable of detecting spatial-frequency structures of 250 cycles/mm measured in the plane of the retina and an optical imaging system,
- an analysis path comprising a device for measuring optical defects with an analysis plane intended to receive a set of light rays backscattered by the retina and means for optically conjugating said analysis plane with a predetermined plane in the input space of said optical imaging system of the imaging path,
- a correction device comprising a correction plane and intended to correct, in said correction plane, the light rays from said emission source and backscattered by the retina as a function of the optical defects measured by the device for measuring optical defects, said correction plane being optically conjugated with said predetermined plane in the input space of said imaging system of the imaging path.

According to the first aspect of the invention, the input pupil of said optical imaging system has a diameter between a first value $\Phi_{min}$ and a second value $\Phi_{max}$, the first value being defined to allow for the detection by said detection device at the central wavelength of said range of imaging wavelengths, of structures of the retina having a spatial frequency of 250 cycles per millimeter, and the second value being less than 5.75 mm.

The applicant has shown notably that, by limiting the diameter of the input pupil of the imaging system, and contrary to received wisdom, the signal-to-noise ratio of the retina image-forming device was improved and the contrast of the microstructures of the retina was thereby enhanced.

Advantageously, the input pupil of the imaging system is positioned in said predetermined plane in the input space of the imaging system, allowing for a better uniformity of the light intensity throughout the field of the image.

According to a variant, the correction device comprises a deformable mirror and the pupil of the deformable mirror defines the physical pupil of the imaging system.

Advantageously, the first value $\Phi_{min}$ is defined as a function of said central wavelength of the range of imaging wavelengths to obtain a theoretical contrast of the imaging system greater than 5% at said spatial frequency of 250 cycles per millimeter. The applicant has in fact demonstrated how, in the retinal imaging devices, the limitation due to the signal-to-noise ratio of the detection made it necessary to have a sufficient aperture of the optic to allow for the detection of fine structures of the retina.

Advantageously, said first value $\Phi_{min}$ is given by the relationship $\Phi_{min}=5000\times\lambda$, where $\lambda$ is the central wavelength of the range of imaging wavelengths.

The applicant has demonstrated that the optimum values of the diameter of the input pupil of the imaging system depend on the range of imaging wavelengths and that it is therefore possible to define ranges of values as a function of the range of wavelengths within which the signal-to-noise ratio will be optimal and resolution will be at its best, regardless of the high-resolution retinal imaging device used.

According to a variant, the central wavelength of the range of imaging wavelengths is between 750 and 1100 nm and the diameter of the input pupil of the imaging system is between 3.75 mm and 5.75 mm. According to a variant, the central wavelength of range of imaging wavelengths is between 500 and 750 nm and the diameter of the input pupil of the imaging system is between 2.5 mm and 5.25 mm. According to a variant, the central wavelength of the range of imaging wavelengths is between 350 and 500 nm and the diameter of the input pupil of the imaging system is between 1.75 mm and 4.25 mm.

According to a variant, the device is of full-field type. The emission source is then an extended source making it possible to illuminate the retina with a given field, and the detection device comprises a matrix detector. The device also comprises a second source for illuminating the retina emitting in a range of analysis wavelengths which advantageously differs from the discrete range of imaging wavelengths, for the analysis of the optical defects by said device for measuring optical defects.

According to another variant, the device is of AOSLO type. The emission source is, according to this variant, a point source making it possible to illuminate the retina with a quasi-point illumination beam and the detection device comprises a confocal detection system. The device also comprises, according to this variant, a system for scanning said illumination beam on the retina.

According to another variant, the device is of OCT type. The emission source is a point source making it possible to illuminate the retina with a quasi-point illumination beam and the detection device comprises an interferometer. The device also comprises, according to this variant, a system for scanning said illumination beam on the retina.

Advantageously, the device for measuring optical defects is an analyzer of Shack-Hartmann type. Such a device makes it possible to analyze, in relation to nominal directions, the variation of the directions of the light rays after having passed through the optical system affected by optical defects. Such a system produces this measurement by virtue, for example, of the arrangement of a matrix detector in the focal plane of a matrix of microlenses. The duly measured variations can be directly used to control the optical defect correction device.

According to a second aspect, the invention relates to a high-resolution retinal imaging method, comprising the emission of at least one light beam for the illumination of the retina of an eye of a subject, in a given range of imaging wavelengths, by means of a light-emission source, the formation of an image of at least a part of the retina illuminated by said light beam emitted in said range of imaging wavelengths on a detection plane of a detection device capable of detecting spatial-frequency structures of 250 cycles/mm measured in the plane of the retina and by means of an optical imaging system with an input pupil of given diameter, the measurement of optical defects by the analysis in a given analysis plane of the optical defects of light rays backscattered by the retina, said analysis plane being conjugated with a predetermined plane of the eye, the correction, in a given correction plane, of the light rays from said emission source and backscattered by the retina as a function of the measured optical defects, said correction plane being optically conjugated with said predetermined plane of the eye.

According to the second aspect of the invention, the diameter of the input pupil of said optical imaging system is between a first value $\Phi_{min}$ and a second value $\Phi_{max}$, the first value being defined to allow for the detection by said detection device at the central wavelength of said range of imaging wavelengths of structures of the retina exhibiting a spatial frequency of 250 cycles per millimeter, and the second value being less than 5.75 mm.

According to a variant, the method is a retinal imaging method of full-field type, also comprising the emission of an analysis light beam in a range of analysis wavelengths for the analysis of the optical defects, and in which the light beam emitted in the range of imaging wavelengths allows for the illumination of the retina with a given field and the formation of the image of said field of the retina is done by means of a matrix detector.

According to a variant, the method is of AOSLO type, also comprising a scanning of said illumination beam of the retina and a confocal detection.

According to a variant, the method is of OCT type, also comprising an interferometric detection.

BRIEF DESCRIPTION OF THE DRAWINGS

Other advantages and features of the invention will become apparent on reading the description, illustrated by the following figures.

DETAILED DESCRIPTION

Figure 2:
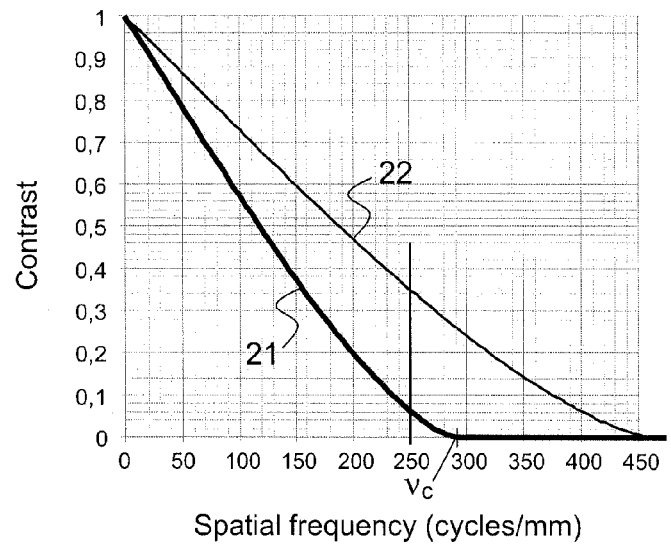
FIG. 2, a curve showing the theoretical trend of MTF as a function of the frequency at a given wavelength (850 nm) for two pupil diameters.

FIG. 2 represents a curve (reference 21) illustrating the modulation transfer function as a function of the frequency (given in cycles per millimeter) in a perfectly corrected optical system limited by diffraction. The value $v_c$ is the cut-off frequency, that is to say the frequency at which the contrast is zero. The cut-off frequency $v_c$ is given by:

$$v_c = \frac{\phi}{\lambda F} \quad (1)$$

Where $\phi$ is the diameter of the input pupil of the optical system, F is the focal length of the optical system and $\lambda$ is the wavelength.

In a retinal imaging system of the type of those described previously, the aim is to form the image of structures of the retina, for example of the cones, photoreceptors with the dimension in proximity to the center of the fovea that is of the order of 2 μm and which are distributed in mosaic fashion with a spatial period of approximately 4 μm. Detecting the structures entails being able to resolve, using the imaging device, a spatial frequency of 250 cycles per millimeter on the retina. If the signal-to-noise ratio of the detector in the optical system were infinite, a minimum diameter of the pupil needed to observe the cones would be given by the equation (1) by taking, for spatial frequency, the frequency corresponding to the elements that are to be observed, i.e. 250 cycles per millimeter. However, in the retinal imaging devices, whether they are of OCT, AOSLO or full-field type, the signal-to-noise ratio is limited by the detection device and the flux backscattered by the retina. A greater minimum diameter of the input pupil—corresponding to a better contrast at the spatial frequency of interest on the curve of FIG. 2—is therefore necessary for the signal to be able to be detected.

It is possible for each of the retinal imaging devices to assess a signal-to-noise ratio, theoretically or by trial and error, according to the detection device used.

Figure 3A:
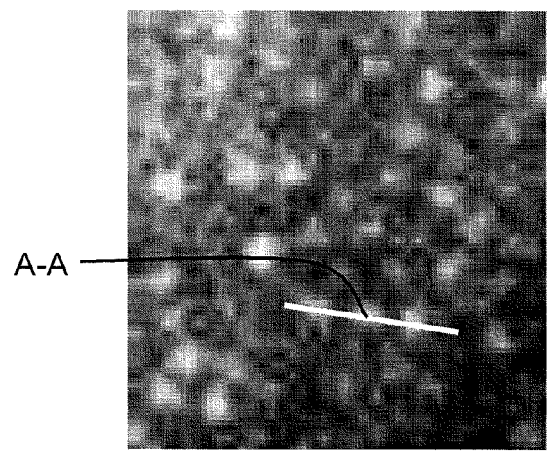
FIG. 3A, an image of the retina measured experimentally on a subject, and FIG. 3B a curve showing the intensity measured on three photoreceptors.
Figure 3B:
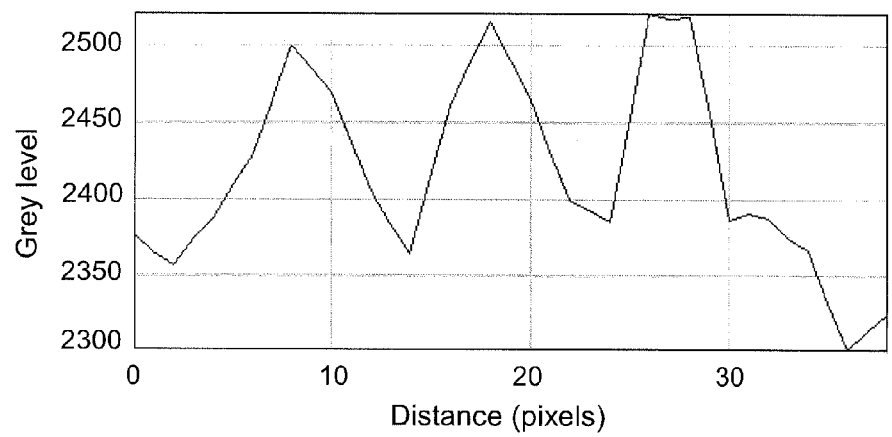

A realistic example of calculation, in the current state of the art, of the signal-to-noise ratio based on experimental data is given in the case of an imaging system of full-field type, illustrated by FIGS. 3A and 3B.

Hereinafter in the description, the expression <<wavelength>> will be used without differentiation to denote the wavelength of a monochromatic light emission source or for the central wavelength of a light emission source with wide spectrum, that is to say emitting in a given range of wavelengths.

The illumination (11, FIG. 1C) of the retina for the purpose of imaging is produced by a lighting source of LED (light-emitting diode) type emitting pulses at 850 nm with a spectral width of 30 nm, of pulse duration 9 ms and recurrence frequency 9.5 Hz. The lit field is 4×4° or 1.2×1.2 mm² approximately on the retina. An average flux of 0.12 mW is sent into the eye, through a pupil of 3 mm diameter. The energy density at the level of the cornea is therefore 1.7 m W/cm². The imaging camera is a 12-bit CCD camera exhibiting, at 850 nm, a quantum efficiency of 0.2, a number of electrons per level of 2.2 e−, a reading noise of 8 e− and a level of obscurity (in the black) of 150 levels. In these conditions, an image (FIG. 3A) was produced on a healthy eye of a 45-year-old person. A set of points corresponding to the photoreceptors on the retina can be seen therein. FIG. 3B represents a cross section produced on three photoreceptors of the retina (line AA in FIG. 3A). It is possible, from FIG. 3B, to calculate the signal-to-noise ratio given by:

$$S/B = \frac{S_u}{\sqrt{S_t + B_l^2}} \quad (2)$$

where $S_u$ is the average useful signal or approximately 150 levels (330 e−) if referring to FIG. 3B, $S_t$ is the total signal, equal to the sum of the useful signal $S_u$ (330 e−) and of the average level of the detected signal excluding background level (2200 levels, or 4840 e−) and $B_1$ is the reading noise (8 e−). A signal-to-noise ratio of 4.6 is thus calculated.

It is then possible to extrapolate what the signal-to-noise ratio would be in the case of greater illumination. In the conditions of use of the camera, the factor which limits the illumination power is linked to ocular safety considerations. More specifically, the factor which has to be taken into account assuming that the incident flux on the eye is increased, is the influence on the cornea. In the above measurement conditions, the influence on the cornea is 1.7 mW/cm² for a permissive limit at 20 mW/cm² for the class I instruments (French standard NF EN ISO 15004-2 2007 on ocular safety). Assuming that the ocular safety limit is not exceeded, an increase in light intensity by a factor of 11.8 is observed, and therefore a signal-to-noise ratio multiplied by a square route factor of 11.8 (disregarding the reading noise which is actually highly negligible compared to the photon noise of the detected signal), i.e. a factor of 3.43 which brings the signal-to-noise ratio to approximately 16. The applicant has thus demonstrated that it is a value of the signal-to-noise ratio which is achievable; such a signal-to-noise ratio makes it possible to detect an object with a contrast of only 1/16, i.e. 6.25%.

Referring now to FIG. 2, it is possible to deduce therefrom a minimum diameter of the input pupil of the system, such that, for the spatial frequency of interest (250 cycles per millimeter), the MTF is at least equal to 6.25%. This corresponds to a spatial frequency $v=0.85\ v_c$. The minimum value $\phi_{min}$ of the diameter of the input pupil of the system is therefore such that:

$$v = 0.85 \frac{\Phi_{min}}{\lambda f} = 250 \quad (3)$$

where f is the focal length of the eye measured in the air (i.e. 17 mm) and $\lambda$, the working wavelength.

Figure 4:
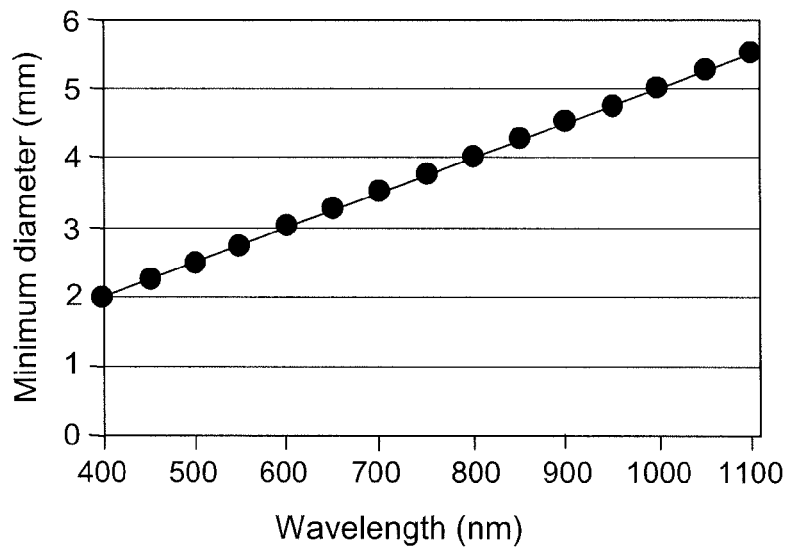
FIG. 4, a curve showing, as a function of the wavelength, the minimum diameter of the input pupil of the imaging system needed to achieve the required resolution of 250 cycles per mm.

FIG. 4 illustrates the minimum diameter of the input pupil of the system as a function of the wavelength, according to the equation 3 obtained with the parameters calculated according to the assumptions described above. It is possible to deduce from this curve, for each wavelength, the minimum value of the diameter of the input pupil needed to distinguish an element of the retina at the spatial frequency of interest. For example, at 850 nm, which is a wavelength conventionally used in retinal imaging for reasons of comfort of the subject, the minimum diameter of the input pupil is 4.25 mm. Generally, by replacing, in the equation (3), the focal length f of the eye by its value measured in the air (17 mm), $\Phi_{min}=5000\times\lambda$ is thus obtained in this example.

A calculation of the maximum signal-to-noise ratio linked to the detection device can be performed for the other retinal imaging systems. Thus, for example, in a system of SLO type, it has been demonstrated that the signal-to-noise ratio could reach values of 10 to 15 depending on the size of the confocal hole, i.e. of the same order of magnitude as that reached with the systems of full-field type.

Whatever the imaging technique, the applicant has thus demonstrated that it is realistic to dimension the input pupil of the imaging system by choosing a minimum diameter such that the theoretical contrast obtained is greater than 5%, corresponding to a signal-to-noise ratio on a detection subsystem of the system of less than 20.

Whatever the imaging technique chosen, it is known that the choice of greater input pupil diameters theoretically makes it possible to view the structures of the retina with a better contrast. Not only because, by increasing the useful flux, the value of the signal-to-noise ratio is theoretically increased, but also because, with a larger input pupil, the response of the optic at high spatial frequencies is better. Thus, with reference to FIG. 2 and continuing with the assumption of a working wavelength at 850 nm, the choice of a pupil of 7 mm diameter compared to a pupil of 4.25 mm diameter would make it possible to increase the cut-off frequency and therefore the value of the theoretical contrast by a factor close to 6 (changing from 6 to 35% contrast) for the frequency of 250 cycles/mm (curve 22 of FIG. 2).

Contrary to this first analysis, the applicant has shown, both theoretically and experimentally, that there was a maximum value of the size of the input pupil beyond which the signal-to-noise ratio degraded, and with it, the contrast of the resolution of the system.

A first reason highlighted by the applicant to explain the deterioration of the signal-to-noise ratio is the Stiles-Crawford effect, described for example in the paper by Jan van de Kraats and Dirk van Norren ("Directional and nondirectional spectral reflection from the human fovea", Journal of Biomedical Optics 13(2), 024010 (March/April 2008).

Figure 5:
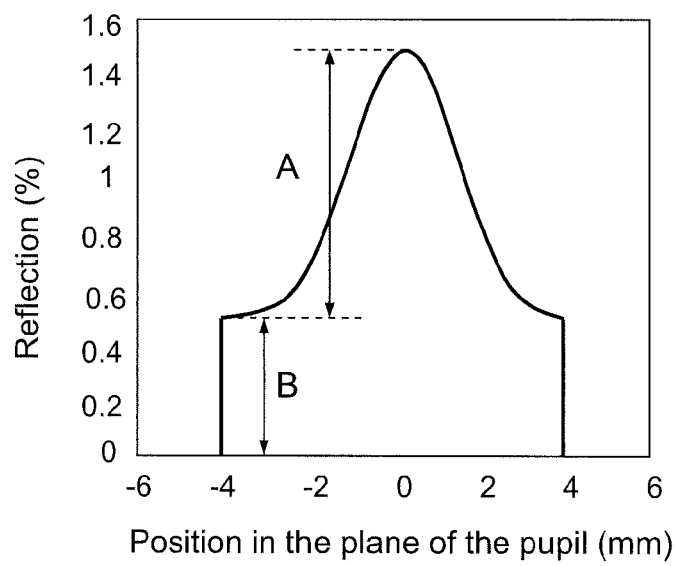
FIG. 5, the curve showing the distribution of the light energy backscattered by the retina as a function of the position in the plane of the pupil.

This paper describes the directional behavior of the layer of the photoreceptors of the retina. The signal backscattered by the retina has a non-directional component derived from the layers of the retina situated upstream and downstream of the layer of the photoreceptors and has a directional component derived from the layer of the photoreceptors. It thus emerges that the non-directional component does not convey the useful signal (it mainly constitutes the noise); furthermore, it changes with the useful surface of the pupil, and therefore with the square of the diameter the pupil). The directional component derived from the layer of the photoreceptors constitutes the useful signal; its energy distribution in the pupil exhibits a Gaussian form. Because of this, the directional component does not change as quickly as the non-directional component when the pupil varies. It follows, as is described in more detail below, that, when the pupil increases, the non-directional component linked to the noise increases more quickly than the directional component (the signal). FIG. 5, taken from the paper by Jan van de Kraats et al., shows the directional (A) and non-directional (B) contribution of the light backscattered by the retina measured at the level of the pupil of the eye.

Figure 1A:
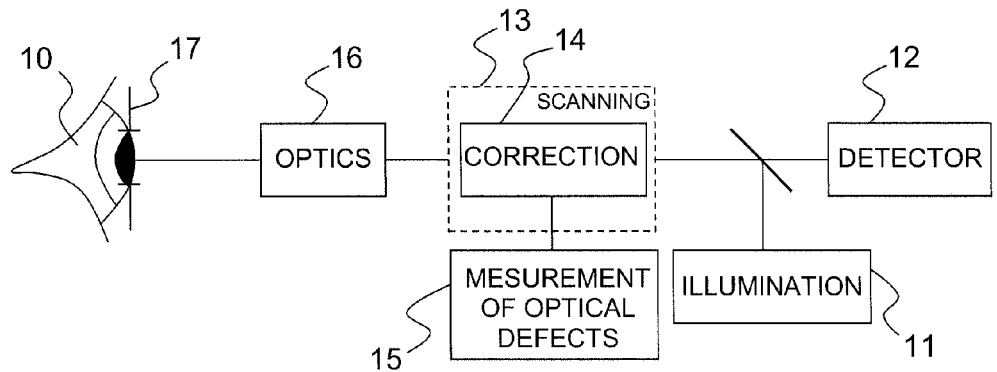
FIGS. 1A to 1C, (already described), theoretical block diagrams of retinal imaging systems known from the prior art.
Figure 1B:
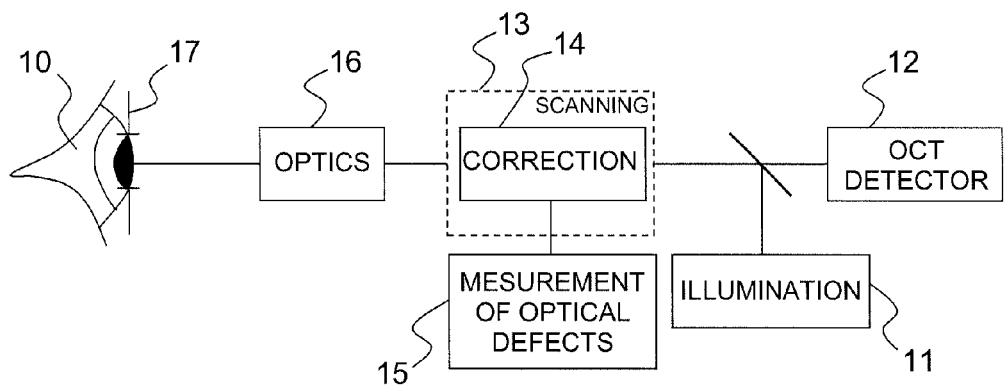
Figure 1C:
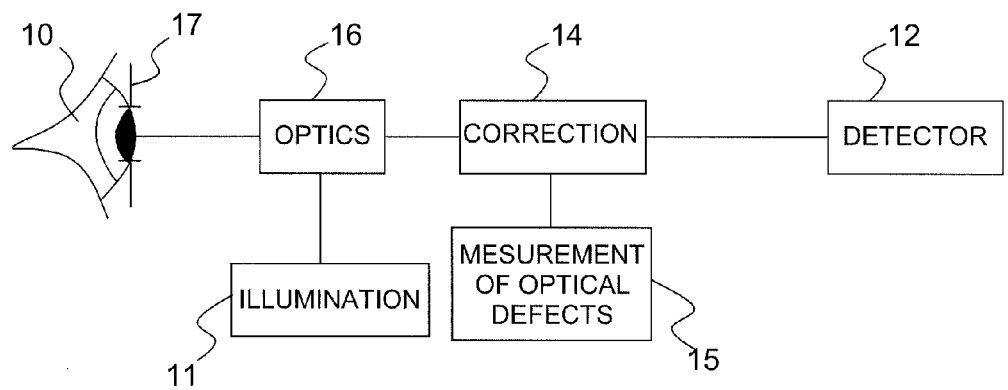

The deterioration of the signal-to-noise ratio is first of all explained with reference to a retinal imaging system of full field type as illustrated in FIG. 1C.

The expression of the distribution of the energy E(r) backscattered by the retina in the pupil is approximated by:

$$E(r) = B + A \exp(-2.3 \, yr^2) \qquad (4)$$

where B is the amplitude of the non-directional component (dependent on the wavelength), A is the amplitude of the directional component and also depends on the wavelength and y is the "directionality" coefficient and is dependent on the wavelength according to the formula:

$$y = 0.05 + 0.097 \times \left(\frac{500}{\lambda}\right)^2 \qquad (5)$$

The integrated signal on the pupil is therefore, for the non-directional component (CND):

$$CND = B \times \pi \times r_{pup}^2 \qquad (6)$$

where $r_{pup}$ is the radius of the pupil.

And for the directional component CD which constitutes the signal:

$$\int_0^{2\pi} \int_0^{r_{pup}} A e^{-2.3 \ast y \ast r^2} r \cdot dr \cdot d\theta = \frac{A \cdot \pi}{2.3 \ast y} \left(1 - e^{-2.3 \ast y \ast r_{pup}^2}\right)$$

The signal-to-noise ratio SNR is given by:

$$SNR = \frac{CD}{\sqrt{CND + CD}}$$

or the equation (7) below:

$$SNR = \frac{A\sqrt{\pi}}{2.3 \ast y \ast \sqrt{B}} \ast \frac{1 - e^{-2.3 \ast y \ast r_{pup}^2}}{\sqrt{r_{pup}^2 + \frac{A}{B \ast 2.3 \ast y}\left(1 - e^{-2.3 \ast y \ast r_{pup}^2}\right)}}$$

The signal-to-noise ratio therefore depends on $r_{pup}$. For a fixed wavelength, the ratio A/B is fixed. The equation (7) shows that the trend, as a function of $r_{pup}$, of the normalized signal-to-noise ratio does not depend on A or B but only on the ratio A/B.

For a wavelength of 850 nm, it can be shown that y=0.09 and A/B=0.1 (this value comes from the paper by Jan van de Kraats et al. and is confirmed by experience).

Figure 6A:
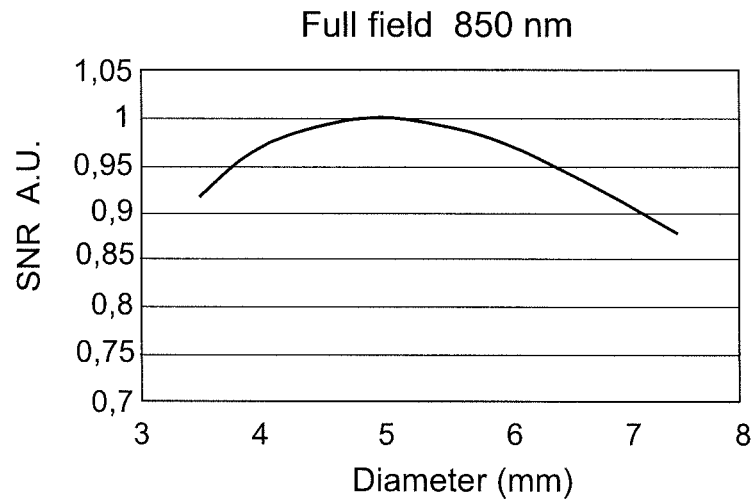
FIGS. 6A and 6B, curves showing the variation of the normalized signal-to-noise ratio as a function of the diameter of the pupil in a retinal imaging device of full-field type, in the near infrared (850 nm) and in the visible (550 nm), respectively.

The normalized curve of the signal-to-noise ratio that is thus obtained is illustrated in FIG. 6A. It can be seen on this curve that the signal-to-noise ratio, contrary to received wisdom, passes through a maximum value of the diameter of the input pupil around 5 mm beyond which it decreases.

Figure 6B:
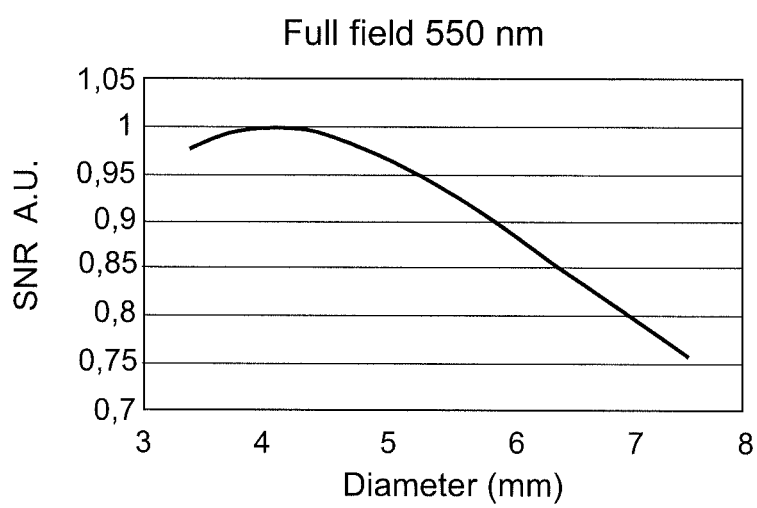

For a wavelength of 550 nm, y=0.147 and A/B=0.5 approximately (here again, this value comes from the paper by Jan van de Kraats et al and can be confirmed by experience). The normalized curve of the signal-to-noise ratio that is thus obtained is illustrated in FIG. 6B. Here again a decrease in the signal-to-noise ratio is observed when the diameter of the pupil increases beyond approximately 4 mm.

The effect of the diameter of the pupil can be highlighted in the same way in the case of retinal imaging systems of OCT or AOSLO type.

The expression of the distribution of the energy backscattered by the retina in the pupil is given by the equation (4) above. However, the confocal effect in the OCT or SLO techniques reduces, notably on the detector, the transmission of the non-directional component of the flux backscattered by the retina because the layers of the retina which backscatter this component are situated above or below the layer of the photoreceptors which is the layer brought into focus on the plane of the hole of the confocal system.

The signal-to-noise ratio of the flux backscattered by the retina is expressed in the same way as in the case of the full field system, namely, it is given by the equation (7) above. The difference lies in the ratio A/B.

In order to evaluate the differential reflectance of the retinal layers, it is possible, for example, to use a commercial OCT system which makes it possible to obtain the information on the rate of reflectance of each layer of the retina. Once this information is available, a calculation is made as to what is the confocal effect as a function of the size of the hole of the confocal system (hole where a fiber input). Once this diameter of the hole is defined, the solid angle by which the image of the confocal hole is seen by each of the layers of the retina ($\Omega_{pinhole}$) is determined and the solid angle by which the pupil of the eye is seen by each of the layers of the retina ($\Omega_{pupil}$) is then calculated. The solid angle that limits the arrival of the light flux originating from each of the layers of the retina will be the smaller of these two solid angles.

The value of these solid angles depends on the depth z of the layer. By convention, z=0 at the level of the layer of the photoreceptors. In order to calculate the solid angles, the following relationship will be used, making it possible to calculate the solid angle by which a disc of radius R is seen at a distance d from the point of observation:

$$\Omega = 2\pi\left(1 - \frac{d}{\sqrt{d^2 + R^2}}\right)$$

It is therefore possible to express $\Omega_{pinhole}$ and $\Omega_{pupil}$ as a function of z, of the diameter $\Phi_{pinhole}$ of the confocal hole, of the diameter $\Phi_{pupil}$ of the pupil and of the focal length f of the eye in the air (17 mm):

$$\Omega_{pinhole} = 2\pi\left(1 - \frac{z}{\sqrt{z^2 + \frac{\phi_{pinhole}^2}{4}}}\right)$$

$$\Omega_{pupille} = 2\pi\left(1 - \frac{f + z}{\sqrt{(f+z)^2 + \frac{\phi_{pupille}^2}{4}}}\right)$$

Figure 7A:
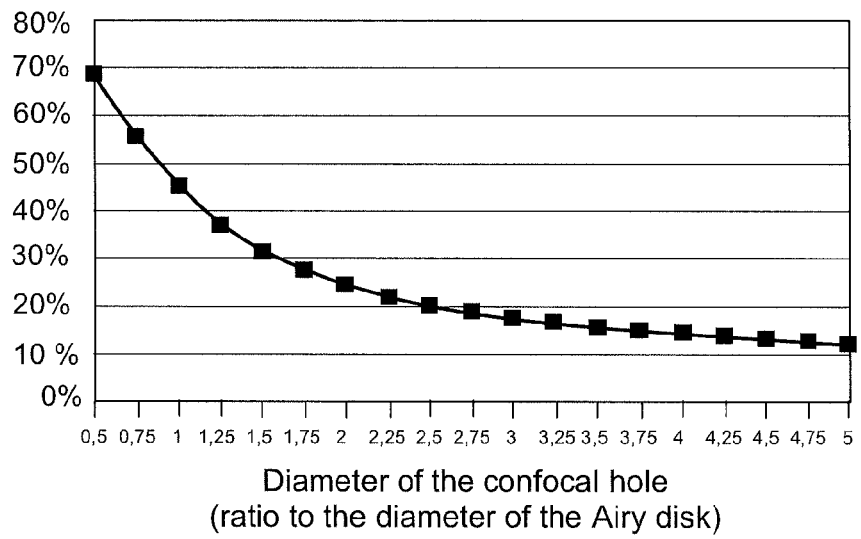
FIG. 7A, a curve showing, in a retinal imaging system of SLO type, the percentage of light originating from the layer of the photoreceptors as a function of the total light backscattered by the retina, as a function of the diameter of the confocal detection hole.

It is then possible to calculate the solid angle of work of the confocal system at the minimum of the solid angles $\Omega_{pinhole}(z)$ and $\Omega_{pupil}(z)$ for each of the layers of the retina that can be seen on the OCT profile (or z is the distance between the layer of the photoreceptors and the layer concerned). By combining this information with the information on the rate of reflectance of each layer of the retina, a curve is obtained which gives the percentage flux backscattered by the layer of the photoreceptors relative to the total flux detected as a function of the size of the confocal hole (expressed as a number of times the diffraction limit). Such a curve is, represented in FIG. 7A. This curve provides direct access to the ratio A/B which is a vital criterion in determining the trend of the normalized signal-to-noise ratio. If the case that is most commonly used these days in the SLO systems where the diameter of the hole of the confocal system is substantially equal to the diameter of the Airy spot, is considered, a ratio A/(A+B)=0.45 is obtained, which means that A/B=0.82.

Figure 7B:
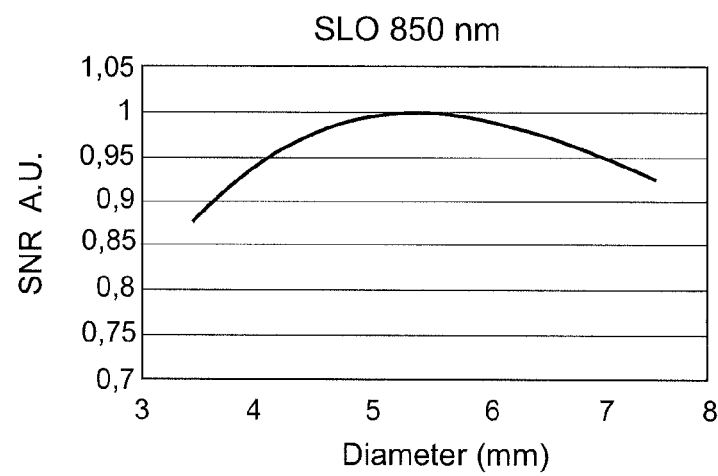
FIG. 7B, a curve showing the variation of the normalized signal-to-noise ratio as a function of the diameter of the pupil in a retinal imaging device of SLO type, in the near infrared (850 nm).

The normalized curve of the signal-to-noise ratio that is thus obtained for an AOSLO system at 850 nm is illustrated in FIG. 7B (y=0.09 and A/B=0.82). A decrease in the signal-to-noise ratio is observed at 850 nm when the diameter of the pupil increased beyond approximately 5.5 mm.

Figure 8A:
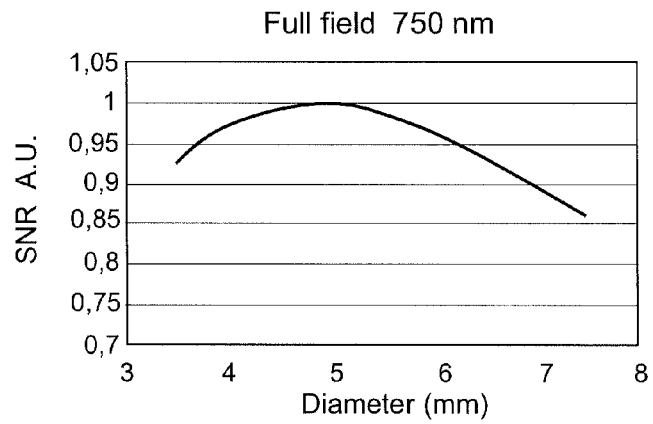
FIGS. 8A to 8F, curves showing the variation of the normalized signal-to-noise ratio as a function of the diameter of the pupil and in retinal imaging devices of full-field or SLO type, at different wavelengths.
Figure 8B:
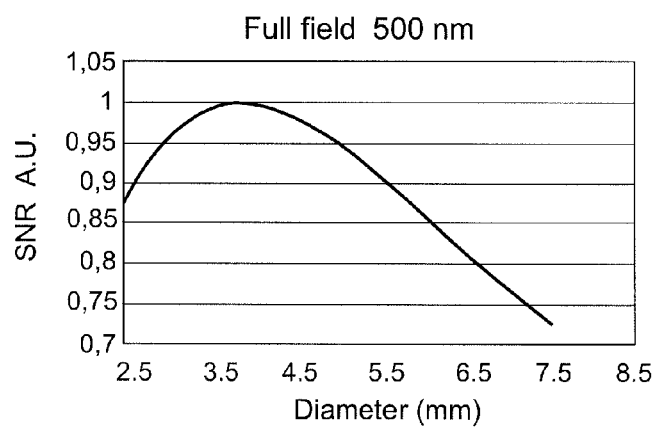
Figure 8C:
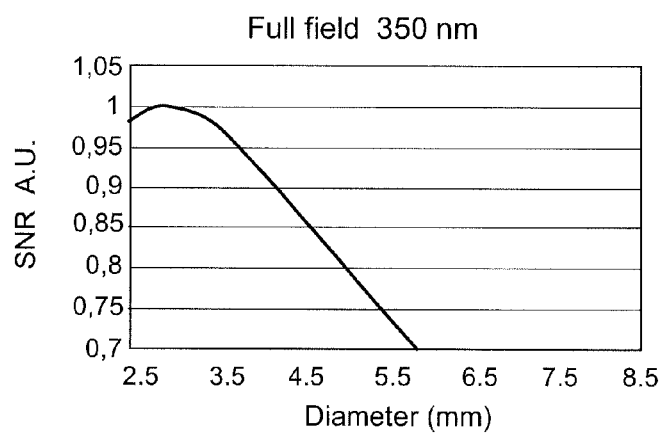
Figure 8D:
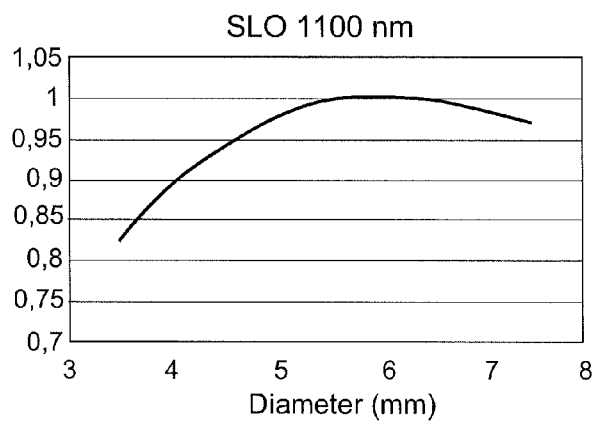
Figure 8E:
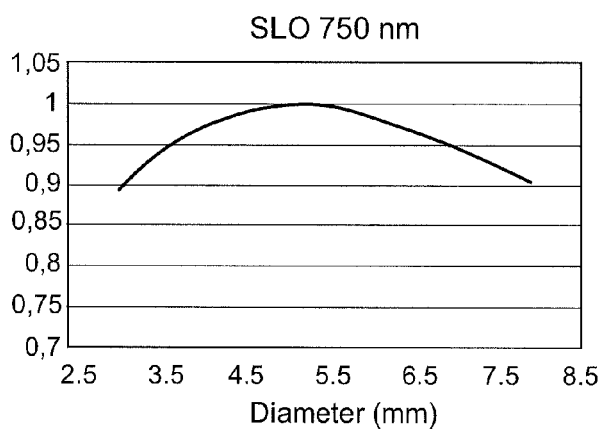
Figure 8F:
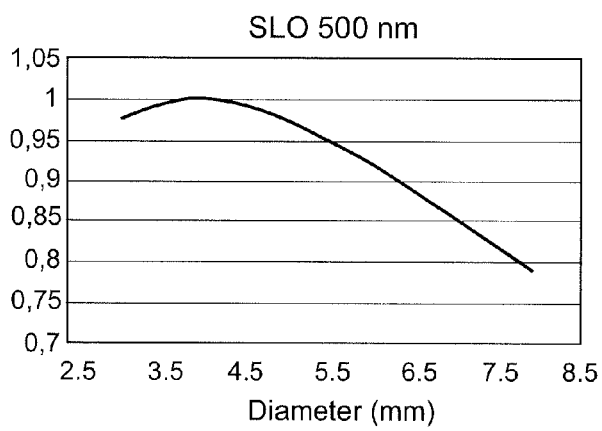

The applicant has thus determined the curves that give, as a function of the value of the diameter of the input pupil of the imaging system, the normalized value of the signal-to-noise ratio, in the case of full-field (FIGS. 8A to 8B) and SLO (FIGS. 8D to 8F) retinal imaging devices. These curves are determined for different imaging wavelengths, respectively 750 nm, 500 nm and 350 nm for the curves 8A to 8C and 1100 nm, 750 nm and 500 nm for the curves 8D to 8F. These curves reveal the value of the diameter of the input pupil from which the normalized signal-to-noise ratio decreases.

Thus, whatever the technique used, the applicant has demonstrated the appearance of a degradation of the signal-to-noise ratio beyond a diameter of the input pupil whose value depends on the wavelength. Typically, in the near infrared (between 750 nm and 1100 nm), the signal-to-noise ratio begins to be degraded for pupil diameters greater than values between 5 and 6 mm. In the visible (between 500 nm and 750 nm), the signal-to-noise ratio begins to be degraded for pupil diameters greater than values between 4 and 5.25 mm. In the "blue" spectral domain (between 350 nm and 500 nm) the signal-to-noise ratio begins to be degraded for pupil diameters greater than values between 3 and 4.25 mm.

A second reason highlighted by the applicant for explaining the deterioration of the signal-to-noise ratio is the presence, in a large number of subjects, and in particular elderly subjects who are the most affected by retinal diseases, of intra-ocular implants. The surgical intervention for the treatment of a cataract in fact consists in removing the opaque crystalline lens, and replacing it with an artificial crystalline lens (intra-ocular implant) which takes its place in the "envelope" of the crystalline lens (called capsule) left partially in place during the intervention (extracapsular extraction). In surgical terms, a senile cataract operation therefore comprises the extracapsular extraction of the lateralized crystalline lens (right or left) by ultrasonic phacoemulsification with conservation of the posterior capsule and the fitting of an intracapsular implant. The useful size of the intra-ocular implant is limited by the contour of the circular hole made in the capsule (capsulo-rhexis) whose diameter is at most 5 mm. Brought into the output space of the eye (that is to say by taking into account the enlargement provided by the cornea), which is also the input space of the imaging system, the maximum useful size is 5.75 mm.

Thus, it appears that a limitation to 5.75 mm of the input pupil of the imaging system is advantageous for the quality of the image, regardless of the wavelength used for the illumination of the retina. In practice, any ray arriving outside this diameter of 5.75 mm will be blocked regardless of its wavelength.

Figure 9:
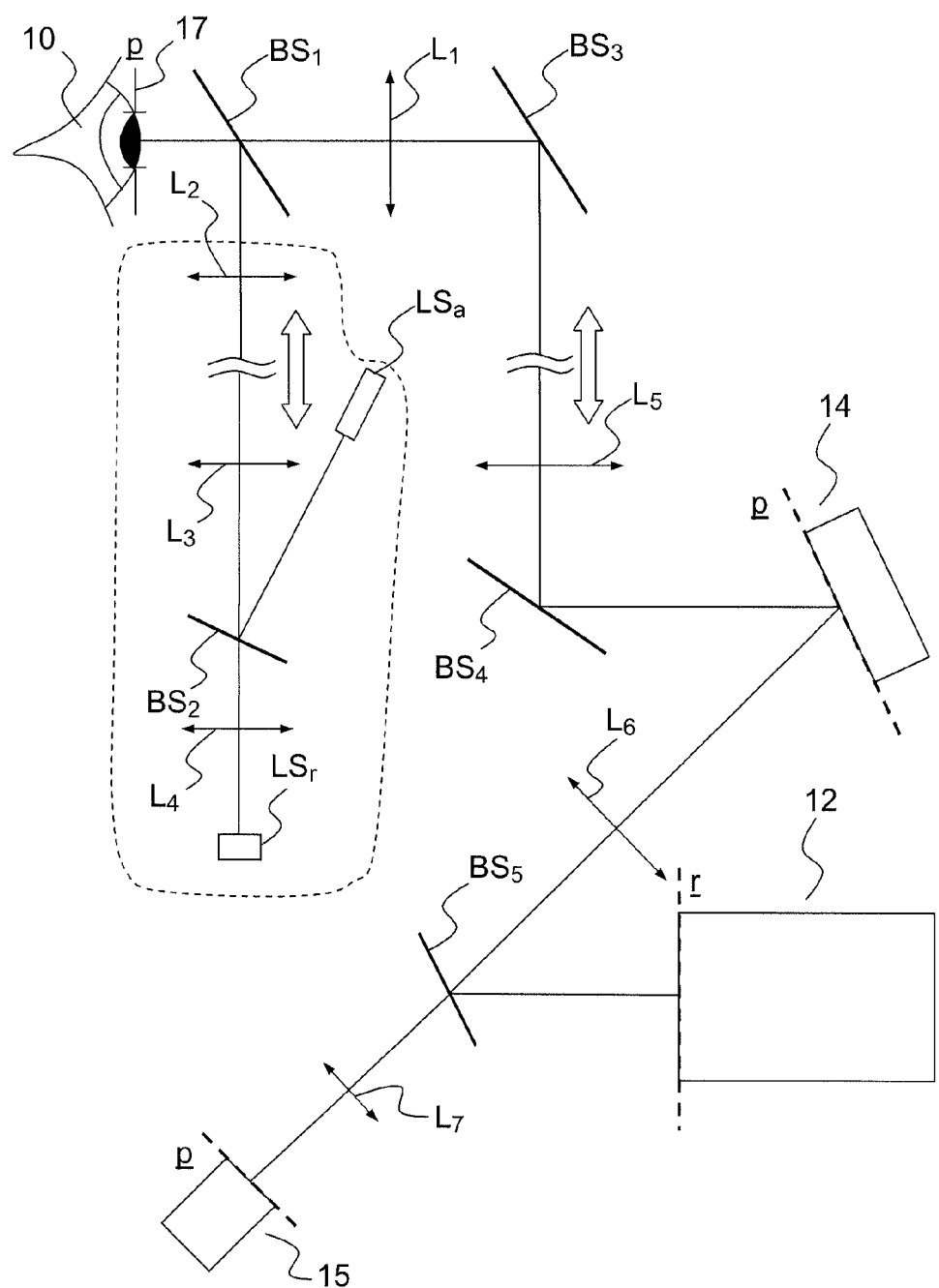
FIG. 9, an example of implementation of a retinal imaging system of full-field type, according to the invention.

As an illustration, FIG. 9 represents an example of a high-resolution retinal imaging device according to an exemplary embodiment of the invention based on full-field technology, also called 'flood' technology. In FIG. 9, only the elements of the device that are necessary to an understanding of the invention are representated. The imaging device comprises an illumination block 11, with a first source $LS_r$ of emission of a light beam intended to illuminate the retina of an eye 10 of a subject in order to form an image thereof by means of the detector block 12. This source is extended, making it possible to illuminate the retina of the eye with a given field, typically 4°×4° to form a so-called "full-field" image. Advantageously, the source of illumination of the retina $LS_r$ has a wavelength in the near infrared, typically between 750 and 1100 nm, a range of wavelengths that offer the subject greater ocular comfort and for which the length of penetration into the layers of the retina is greater. According to a variant, the wavelength of the source of illumination of the retina $LS_r$ can also be in the visible to produce color images of the retina. Wavelengths in the blue, typically between 350 and 500 nm, can also be used to visualize the bundles of nerve fibers in the case of glaucoma for example. The source $LS_r$ is, for example, an LED or a lamp provided with a filter. The illumination block 11 also comprises a second emission source $LS_a$ of illumination of the retina intended for the analysis of the optical defects of the imaging system. Unlike the emission source $LS_a$ intended for the imaging, the emission source $LS_a$ is a point source, making it possible to form a secondary source point on the retina of the eye of the subject. Typically, the central wavelength of the emission source $LS_a$ for the analysis of the optical defects is 750 nm. Such a wavelength is comfortable for the subject and as near as possible to the imaging wavelength. Preferably, the wavelength of the source $LS_a$ is different from that of the source LSr for reasons of separation of the optical paths between the measurement of the optical defects and the imaging of the retina. The source $LS_a$ is, for example, a laser diode or a super light-emitting diode SLED. A set of splitter plates $BS_1$, $BS_2$, makes it possible to send to the eye 10 of the subject the light beams emitted by the sources $LS_r$ and $LS_a$. A set of optical elements $L_2$, $L_3$, $L_4$, are used to form, from the emission sources, incident collimated beams on the pupil of the eye. The image of the retina is formed on the detector block 12, comprising, for example, an imaging camera of CCD type, by means of an imaging system notably comprising a set of optical elements referenced $L_1$, $L_5$, $L_6$ in FIG. 9. The imaging system has an input pupil intended to be positioned in a predetermined plane 17 of the eye, for example the pupil plane. In FIG. 9, the planes referenced by the letter "r" correspond to the planes optically conjugated with the plane of the retina, whereas the planes referenced by the letter "p" correspond to the planes optically conjugated with said predetermined plane 17. The retinal imaging device also comprises a device 15 for analyzing optical defects. This involves analyzing all the disturbances that the light rays are subjected to between the retina and the detector. The optical defects within the meaning of this description therefore comprise the defects brought about by the optical system of the eye but also by the part of the optical imaging system that is common with the analysis path. The device for analyzing the optical defects is, for example, an analyzer of Shack-Hartmann type (HASO® 32-eye Imagine Eyes®), comprising an analysis plane formed by a set of microlenses and a detector positioned in the focal plane of the microlenses. The analysis plane is advantageously optically conjugated with plane 17 of the input pupil of the imaging system by means of the optical elements $L_1$, $L_5$, $L_6$ and an additional optical element $L_7$. A computer (not represented) makes it possible to determine the optical defects of the system and to send a correction command to the correction device 14, for example a deformable mirror of the mirao 52-e Imagine Eyes® type. Advantageously, the computer associated with the Shack-Hartmann analyser, determines, in relation to nominal directions, the variation of the directions of the light rays that have passed through the optical system affected by optical defects. The variations that are thus measured can be directly used to control the deformable mirror. The plane of the deformable mirror is also optically conjugated with the plane 17 of the input pupil of the imaging system. A set of splitter plates, referenced $BS_4$, $BS_5$, $BS_6$, in FIG. 9, make it possible to direct the light rays from the emission sources $LS_r$ and $LS_a$ and backscattered by the retina onto the deformable mirror 12 then respectively to the detector 12 and the analyzer 15, respectively forming the imaging and analysis beams. According to a variant, the input pupil 17 of the imaging device is an image of the pupil of the deformable mirror.

A clinical study was conducted to experimentally check the improvement of the quality of the image with the optimization of the size of the input pupil of the imaging system. The protocol put in place was based, among other things, on the measurement of the retina with two high-resolution retinal imaging devices of full-field type incorporating an adaptive optical system. These devices are of the type of those described in FIG. 9, but one of the two devices has an input pupil of 7.5 mm diameter, the other an input pupil of 5 mm. The imaging wavelength is 850 nm in both devices. The overall architecture as well as all the components are identical (same characteristics) for the two devices. In both cases, the pupil of the corrector component, in this case a mirao 52e (Imagine Eyes®) deformable mirror, represents the physical pupil of the imaging system. The only difference between the two devices therefore lies in the optical enlargement between the pupil of the deformable mirror and the eye. In the case of the system of 7.5 mm pupil diameter, the enlargement is 2 between the pupil of the eye and the deformable mirror (15 mm pupil diameter) and in the case of the system with an input pupil diameter of 5 mm, the enlargement is 3.

The number of eyes imaged in the context of this study was 19. For each eye, three images were produced at the level of the layer of the photoreceptors for 2 degrees and 5 degrees of temporal eccentricity relative to the center of the fovea and with both imaging devices. In all, six images per eye and per device were therefore produced. The comparison was founded on a notation system based on the visibility of the photoreceptors on a scale of five grades (scoring 5 for the best and 1 for the least good). The scoring was done by four observers. The results have shown that, on average, the images produced with the system with a 5 mm input pupil diameter have scores 1 grade better than those produced with the system with 7.5 mm input pupil diameter. Compared on a one-to-one basis (the best of the three images for the same eye, same position in the retina), the 19 images produced with the system with 5 mm input pupil diameter are better in 15 cases out of 19, equally good in two cases out of 19 and worse in two cases out of 19 than those produced with the system with 7.5 mm input pupil.

Figure 10A:
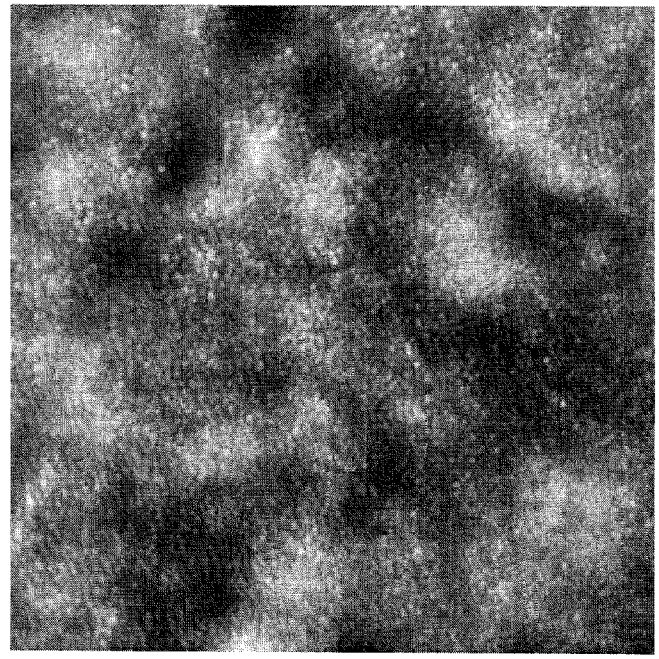
FIGS. 10A and 10B, images of retinas measured in retinal imaging systems full-field type at 850 nm, respectively with a pupil of 7.5 mm and a pupil of 5 mm.
Figure 10B:
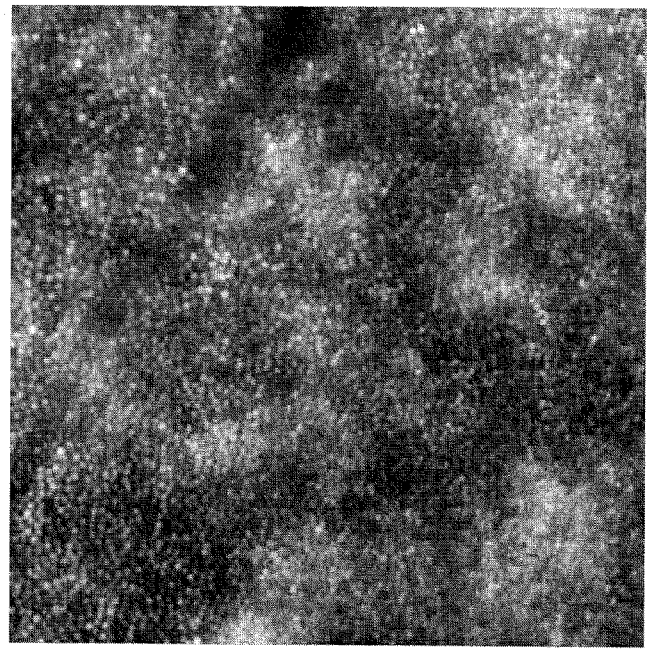

FIGS. 10A and 10B illustrate the result of this study. The two images presented were produced on the same eye (person 58 years old) and at exactly the same point on the retina, with a temporal eccentricity of 2 degrees, with retinal imaging devices in which the retina imaging system on the detector have input pupils of respectively 7.5 and 5 mm. They exhibit 1 grade deviation on the scoring scale in favor of the system with 5 mm input pupil. They are therefore representative of the standard deviation observed between the two devices.

Although described through a certain number of detailed exemplary embodiments, the retinal imaging device and the method according to the invention comprise different variants, modifications and refinements which become obviously apparent to a person skilled in the art, given that these different variants, modifications and refinements form part of the scope of the invention, as defined by the following claims.

The invention claimed is:

1. A high-resolution retinal imaging device, comprising
at least one emission source ($LS_r$) for emitting a light beam for the illumination of a retina of an eye of a subject, emitting in a given range of imaging wavelengths;
a retina imaging path comprising a detection device capable of detecting spatial-frequency structures of 250 cycles/mm measured in the plane of the retina and an optical imaging system;
an analysis path comprising a device for measuring optical defects with an analysis plane intended to receive a set of light rays backscattered by the retina and means for optically conjugating said analysis plane with a predetermined plane in the input space of said optical imaging system; and
a correction device comprising a correction plane and intended to correct, in said correction plane, the light rays from said emission source ($LS_r$) and backscattered by the retina as a function of the optical defects measured by the device for measuring optical defects, said correction plane being optically conjugated with said predetermined plane in the input space of the optical imaging system of the imaging path,
wherein:
the input pupil of said optical imaging system has a diameter between a first value $\Phi_{min}$ and a second value $\Phi_{max}$, the first value being defined to allow for the detection by said detection device at the central wavelength of said range of imaging wavelengths, of structures of the retina having a spatial frequency of 250 cycles per millimeter, and the second value being less than 5.75 mm.

2. The device as claimed in claim 1, wherein said input pupil of the imaging system is positioned in said predetermined plane of the input space of said imaging system.

3. The device as claimed in claim 1, wherein the correction device comprises a deformable mirror, the pupil of which defines the physical pupil of the imaging system.

4. The device as claimed in claim 1, wherein said first value $\Phi_{min}$ is defined as a function of said central wavelength of the range of imaging wavelengths to obtain a theoretical contrast of the imaging system greater than 5% at said spatial frequency of 250 cycles per millimeter.

5. The device as claimed in claim 4, wherein said first value $\Phi_{min}$ is given by a relationship $\Phi_{min}=5000\times\lambda$, where $\lambda$ is said central wavelength of the range of imaging wavelengths.

6. The device as claimed in claim 1, wherein said central wavelength of the range of imaging wavelengths is between 750 and 1100 nm and the diameter of the input pupil of the imaging system is between 3.75 mm and 5.75 mm.

7. The device as claimed in claim 1, wherein said central wavelength of the range of imaging wavelengths is between 500 and 750 nm and the diameter of the input pupil of the imaging system is between 2.5 mm and 5.25 mm.

8. The device as claimed in claim 1, wherein said central wavelength of the range of imaging wavelengths is between 350 and 500 nm and the diameter of the input pupil of the imaging system is between 1.75 mm and 4.25 mm.

9. The device as claimed in claim 1, wherein the device is a full-field device, said emission source ($LS_r$) being an extended source making it possible to illuminate the retina with a given field, and the detection device comprising a matrix detector, the device also comprising a second emission source ($LS_a$) for illuminating the retina emitting in a given discrete range of analysis wavelengths, for the analysis of the optical defects by said device for measuring optical defects.

10. The device as claimed in claim 1, wherein the device is of Adaptive Optics Scanning Laser Ophthalmoscopy (AOSLO) device, said emission source being a point source making it possible to illuminate the retina with a quasi-point illumination beam and the detection device comprising a confocal detection system, the device also comprising a system for scanning said illumination beam on the retina.

11. The device as claimed in claim 1, wherein the device is Optical Coherence Tomography (OCT) device, said emission source being a point source making it possible to illuminate the retina with a quasi-point illumination beam and the detection device comprising an interferometer, the device further comprising a system for scanning said illumination beam on the retina.

12. The device as claimed in claim 1, wherein the device for measuring optical defects is a Shack-Hartmann analyzer.

13. A high-resolution retinal imaging method, comprising:
emission of at least one light beam for the illumination of a retina of an eye of a subject, in a given range of imaging wavelengths, by a light-emission source;
formation of an image of at least a part of the retina illuminated by said light beam emitted in said range of imaging wavelengths on a detection plane of a detection device capable of detecting spatial-frequency structures of 250 cycles/mm measured in the plane of the retina and by an optical imaging system with an input pupil of given diameter;
measurement of optical defects by the analysis in a given analysis plane of the optical defects of light rays backscattered by the retina, said analysis plane being optically conjugated with a predetermined plane of the eye; and
correction, in a given correction plane, of the light rays from said emission source and backscattered by the retina as a function of the measured optical defects, said correction plane being optically conjugated with said predetermined plane of the eye, wherein:
the diameter of the input pupil of said optical imaging system is between a first value $\Phi_{min}$ and a second value $\Phi_{max}$, the first value being defined to allow for the detection by said detection device at the central wavelength of said range of imaging wavelengths of structures of the retina exhibiting a spatial frequency of 250 cycles per millimeter, and the second value being less than 5.75 mm.

14. The retinal imaging method as claimed in claim 13, wherein the device is a full-field device, further comprising the emission of an analysis light beam in a given range of analysis wavelengths for the analysis of the optical defects, and in which the light beam at said central wavelength of the range of imaging wavelengths allows for the illumination of the retina with a given field and the formation of the image of said field of the retina is done by a matrix detector.

15. The retinal imaging method as claimed in claim 13, Adaptive Optics Scanning Laser Ophthalmoscopy (AOSLO) device, further comprising a scanning of said illumination beam of the retina and a confocal detection.

16. The retinal imaging method as claimed in claim 13, of Optical Coherence Tomography (OCT) device, further comprising an interferometric detection.

* * * * *